/

US010322100B2

(12) United States Patent
Baggot

(10) Patent No.: US 10,322,100 B2
(45) Date of Patent: *Jun. 18, 2019

(54) MATERNAL CHELATION FOR EMBRYO, FETAL AND INFANT BENEFIT

(71) Applicant: Patrick James Baggot, Monterey Park, CA (US)

(72) Inventor: Patrick James Baggot, Monterey Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/437,094

(22) Filed: Feb. 20, 2017

(65) Prior Publication Data

US 2017/0157078 A1    Jun. 8, 2017

Related U.S. Application Data

(60) Continuation of application No. 14/881,273, filed on Oct. 13, 2015, now Pat. No. 9,700,533, which is a division of application No. 11/536,795, filed on Sep. 29, 2006, now Pat. No. 9,186,376.

(60) Provisional application No. 60/722,907, filed on Sep. 30, 2005.

(51) Int. Cl.

| | |
|---|---|
| *A61K 31/185* | (2006.01) |
| *A61K 31/194* | (2006.01) |
| *A61K 31/727* | (2006.01) |
| *A61K 31/198* | (2006.01) |
| *G01N 33/493* | (2006.01) |
| *G01N 33/84* | (2006.01) |

(52) U.S. Cl.
CPC .......... *A61K 31/194* (2013.01); *A61K 31/185* (2013.01); *A61K 31/198* (2013.01); *A61K 31/727* (2013.01); *G01N 33/493* (2013.01); *G01N 33/84* (2013.01); *G01N 2800/368* (2013.01)

(58) Field of Classification Search
CPC ............................ A61K 31/185; A61K 31/194
USPC ........................................................ 514/578
See application file for complete search history.

(56) References Cited

U.S. PATENT DOCUMENTS

| 6,114,387 | A | 9/2000 | Cutler | |
|---|---|---|---|---|
| 9,186,376 | B2 * | 11/2015 | Baggot | A61K 31/727 |
| 9,700,533 | B2 * | 7/2017 | Baggot | A61K 31/727 |
| 2006/0058241 | A1 | 3/2006 | Geier et al. | |

OTHER PUBLICATIONS

Palagiano's CAS: 11395693, 2001.*
Risher et al., Neuro Toxicology, 2005, 26:6091-699.*
Crichton et al., Eur J. Biochem, 1987, 164: 485.*
Needleman, H.I. et al.; "Lead and IQ Scores": 1985; A Reanalysis: Science, 227:701-704.
Needleman, H.I. et al.; "Deficits in Psychologic and Classroom Performance of Children with Elevated Dentine Lead Levels"; 1979; N. Eng. J. Med. 300:689-695.
Domingo, J.L., "Developmental Toxicity of metal chelating agents." 1998; Reproductive toxicology vol. 12, No. 5, 499-510.
Rice, D.C.; "Developmental Lead Exposure, Neurobehavioral Consequences in Handbook of Developmental Neurotoxicology"; Academic Press; 539-557 (1998).
Volpe, J.J.; "Neurology of the Newborn", Fourth Ed.; W.B. Saunders Co.; 217-275.
Bailey, B., "Are There Teratogenic Risks Associated with Antidotes Used in the Acute Management of Poisoned Pregnant Women?"; 2003; Birth Defects Research (Part A); 67:133-140.
Foresight; "Trace Elements and Preconceptual Care"; www.foresight-preconception.org.uk/booklet_traceelements.htm (2006).
Glenville, M.; "Health Professionals' Guide to Preconception Care"; Foresight; www.foresight-preconception.org.uk/booklet_healthproguide.htm (2006).
Janette Roberts, BPharm (Hons); The Foresight Program; "Improving Reproductive and Infant Health Through Periconceptual Care"; Nov. 1995; www.acnem.org/journal/14-2.
Domingo; "Prevention by chelating agents of metal-induced developmental toxicity"; 1995; Reproductive Toxicology; 9(2): 105-113.
Aposhian et al.; "Mobilization of heavy metals by newer, therapeutically useful chelating agents"; 1995; Toxicology; 97: 23-38.
Moutel et al.; "The Perruce decree, an opportunity to question the acceptance of a handicap and the relationship between physicians, justice and society"; 2002; Presse Med. 31(14): 632-5; abstract; PMID: 11995380.
Raymond et al.; "Maternal-fetal lead poisoning from a 15-year-old bullet"; 2002; The Journal of Maternal-Fetal and Neonatal Medicine; 11:63-66.
Das et al.; "Metallic ion concentration during menstrual cycle in normally menstruating women"; 1997; Indian J. Med. Sci.; 51(2):52-4; PubMed abstract; PMID: 9355709.
Lundt et al. CAS: 144:51846, 2005.
Pace's CAS: 11395693, 2001.

* cited by examiner

*Primary Examiner* — Rei Tsang Shiao
(74) *Attorney, Agent, or Firm* — Brendan O. Baggot; Husch Blackwell LLP

(57) ABSTRACT

This invention teaches the use of chelating agents to diagnose and treat metal toxins in a patient. Chelation agents are given to the mother for the benefit of the baby. Metal toxins such as lead, arsenic, mercury, tin, antimony, aluminum and others are known to cause miscarriages, birth defects, maldevelopment of the organs and tissues and maldevelopment of the brain. Chelation treatments of the mother can prevent these problems in the embryo, fetus and infant. Removal of lead and mercury and other toxins allows improved development of the offspring, both during the chelation and after the chelation is discontinued. Determining whether a mother who has just delivered a baby has elevated levels of heavy metals can also be used to identify the elevated metals of the mother as a possible cause of birth defects.

16 Claims, No Drawings

MATERNAL CHELATION FOR EMBRYO, FETAL AND INFANT BENEFIT

CROSS-REFERENCE TO RELATED APPLICATIONS

This application is a continuation of U.S. Utility application Ser. No. 14/881,273, filed on Oct. 13, 2015, which claims priority to U.S. Utility application Ser. No. 11/536,795, filed Sep. 29, 2006, which claims priority to and the benefit of U.S. Provisional Patent Application No. 60/722,907, filed Sep. 30, 2005, the entire contents of all of which are incorporated herein by reference.

BACKGROUND OF THE INVENTION

Field of the Invention

This invention relates generally to the field of medicine, and more particularly to a method of enhancing the embryonic, fetal, conceptus, infant, and human child development by chelation treatment of the mother to remove toxic substances.

Related Art

There are a number of diagnostic methods, treatment regimens and preventative measures that the medical community has encouraged and patients have taken to reduce the occurrences of birth defects, miscarriages, infertility disorders and childhood neurologic dysfunctions. However, even with currently known therapies, there are too many birth defects, miscarriages, infertility disorders and childhood neurologic dysfunctions. As societies moved away from their organic agricultural bases to industrialized manufacturing economies, including the use of chemical pesticides and industrial techniques for farming, the environment in which people live has become less organic and more toxic. Therefore, while industrialized societies greatly improve health care, there are much greater environmental hazards facing people, particularly metal toxins that build up within a person's system. To date, there has not been a comprehensive methodology to diagnose, isolate and remove these metal toxins. Instead, industrialized societies have sought solutions without regard to their environmental toxins.

Birth defects have, in the past, been prevented by the use of folate, by the use of multivitamins, by abstaining from alcohol and harmful drugs, and by avoidance of carotenoids such as vitamin A. Avoidance of carotenotic drugs has also been done. However, birth defects are still too common, with a prevalence of 2 to 4 percent (2%-4%) among live born infants. Most birth defects, approximately 70%, have no known cause.

Miscarriages are also too common with 15% of pregnancies ending in miscarriage, and in the vast majority of cases, no cause is found. Metal toxins can cause birth defects, spontaneous abortion, and/or miscarriage.

Miscarriage is common: as stated previously, approximately 15% of all pregnancies end in miscarriage. Miscarriages can be caused by uterine abnormalities which can be treated with uterine surgery. Miscarriages can be caused by antiphospholipid antibody syndrome, and these have been treated with heparin, aspirin and steroids. Miscarriages can be caused by thrombophilias in which an inherited abnormality of one of the proteins controlling the clotting cascade causes malfunction. Thrombophilias have been treated with anticoagulants such as aspirin and/or heparin. Miscarriage can be caused by diabetes, and treatment of diabetes has reduced the rate of miscarriage. This treatment includes insulin for blood sugar control and metformin for insulin resistance. Miscarriages caused by hypothyroidism can be treated with thyroid replacement.

While it is acknowledged that miscarriages are caused by lead, mercury or other heavy metal toxins, no program has been advanced other than the limited Foresight program. Foresight Great Britain has developed a program for the prevention of birth defects and miscarriage. This program identifies mineral toxicities by means of hair analysis. Metal toxins, when found, are treated with vitamin C, nutrient minerals and multivitamins, and selenium. However, the Foresight program is sub-optimal because it is limited to using hair analysis rather than a provocative chelation or even a blood analysis without a provocative chelation, and it is not expressly directed to quantifying and removing metal toxins using chelation treatments. Accordingly, its recommendations are limited to supplementing the patient's diet with selenium and vitamin C, rather than selecting from a range of chelation treatments that should be considered when toxic metals are identified, particularly including the use of more effective synthetic chelators.

Mental retardation affects approximately 3% of children, and some studies indicate that attention deficit disorder may affect 20%-40% of all children. Mild variants of minimal brain dysfunction, including disorders of auditory and/or visual perception and/or processing, are too common. Minor degrees of abnormal neurologic development can be manifested by behavioral, developmental or other neurologic abnormalities. All told, there is an abundance of childhood neurologic dysfunction which leads to behavioral problems, emotional problems, intellectual problems, lost learning, reduced intelligence and decreased intellectual capacity and job performance.

Diagnosis and treatment of childhood neurologic dysfunction has been largely postnatal and thus too late. Postnatal problems that cause mental deficits include inborn errors of metabolism. These have been diagnosed with urinary amino acids, urinary organic acids, and other biochemical tests postnatally. Chromosomal analysis has enabled the diagnosis of neurologic dysfunctions secondary to chromosomal disorders. Few, if any, treatments are known for chromosomal disorders. No anatomic maldevelopment may be detected by imaging studies of the brain including ultrasound, MRI or CAT scan. Most of these conditions have no known treatment. Genetic syndromes can be identified as a cause of mental retardation by examination and inspection of the affected child, the facial and physical exam findings may suggest one or more genetic syndromes that can be tested for either by DNA methods, by chromosomal methods or by biochemical methods.

Lead poisoning is commonly investigated and detected postnatally by a blood test or occasionally by provocative challenge with a chelation agent. Chelation treatments have long been given to children to remove lead. Chelation agents used on children for removal of lead include DMSA and EDTA. While it is known that lead can accumulate in fetuses antenatally, no program of fetal detoxification has been advocated prenatally because synthetic chelating agents are thought to be teratogenic. However, other work has suggested that studies showing harmful effects of chelators might have been due to a failure in those studies to co-administer mineral supplements to the patient along with the chelators. Thus in those studies the adverse outcomes observed following chelation therapy might have been due to the chelators having leached essential minerals from the patient's body rather than any harmful effects of the chelating chemicals themselves. Nonetheless, chelators have only been given to mothers for severe maternal toxicity but not for fetal benefit. No chelation treatment has ever been done for mothers with lead, mercury, aluminum, or antimony levels that are below what is considered acutely toxic.

Mercury is known to cause cerebral palsy and mental deficits. This was shown from an outbreak of mercury toxicity that occurred in Japan where it has caused Minamata disease. Another outbreak of mercury poisoning occurred in Iraq. Mercury is widely thought to cause autism when injected with vaccinations. For this reason, the mercurial preservative thimerosol has been removed from most vaccinations. Additionally, mercury vapor, which may arise from amalgam dental fillings, is known to cross the placenta and affect the fetus. Other than the Foresight program, there is no program to identify and detoxify preconceptional women, pregnant women, or lactating women so that toxins will not accumulate in the baby and affect embryonic, fetal, neonatal or infant development. Additionally, there is no program to identify similar toxins in men and to detoxify these men with chelation therapies prior to impregnating their partners. The standard of care for improving fetal outcome is prenatal diagnosis. In prenatal diagnosis, ultrasound examinations are done on fetuses. In some cases, chromosomal analysis is done. When problems are detected, termination is offered to the mother. This system has limited effectiveness because: 1. many abnormalities are missed, 2. mild abnormalities are missed, 3. abnormalities of neurological function are usually missed, and 4. many mothers refuse termination when it is offered.

The problems with the above-discussed approach of testing women who are already pregnant are as follows: 1) Prevention of mental deficit by prenatal diagnosis and selective abortion cannot be universally applied and is harmful to the fetus: the resultant death to the fetus is objectionable to many, and, therefore, is often refused; 2) Lead, mercury and almost all teratogens have their greatest effect early in development when the embryo/fetus is most vulnerable and susceptible. Treatment early in the development would have a much more profound beneficial effect than treatment later in development.

There are half as many children in the United States today with intelligence quotients (IQs) above 130 than there were in past generations. The effects of heavy metals, herbicides, pesticides, and organic toxins on early brain development last for decades. Regions with higher infant mortality also have higher rates of emphysema seventy (70) years later. The health of the gravid female during pregnancy makes for healthy babies, adolescents, and adults. The removal of heavy metals by therapeutic chelation of the pregnant woman will likely lead to increased IQ's, increased scores on neurological development tests like the Denver Developmental Exam, and higher scores on standardized tests of the offspring years after the treatment of the gravid female has concluded. Higher order mental and neurologic function include but are not limited to those traits which are well known to lead to higher scores on IQ tests, standardized tests, neurologic ability tests and entrance exams for colleges and professional schools.

As discussed above, the Foresight program is insufficient in its diagnostic evaluation of the patient and in its treatment regimen. While this program has some usefulness, it is too limited of a program for diagnosing and treating symptomatic adults. Given the grave threat posed by metal toxins to the fetus, more aggressive treatment may result in enhancement of neurologic development and performance.

SUMMARY OF THE INVENTION

Reproductive chelation treatments can be given to the mother before conception, during pregnancy and/or during lactation for fetal/embryonic/neonatal benefit. The chelation therapy consists of treating the mother with a chelating agent so as to benefit her offspring. The goals are to remove metal toxins so as to prevent birth defects, miscarriages, suboptimal organ development including brain development and to enhance the neurologic development both during and after pregnancy and lactation.

In one embodiment, the invention is a method of attenuating or preventing human birth defects, spontaneous abortions, infertility and childhood neurological dysfunctions caused by subclinical levels of heavy metals including the steps of identifying the presence of subclinical levels of heavy metals in a fertile human female; calculating a suitable dosage of a synthetic chelating agent; and administering the dosage of the synthetic chelating agent to the pregnant human female.

In another aspect, the invention is a method of attenuating or preventing human birth defects, miscarriages, infertility and childhood neurological dysfunctions caused by subclinical levels of heavy metals in a pregnant human, including the steps of identifying the presence of subclinical levels of heavy metals in the pregnant human; calculating a suitable dosage of a proteinaceous chelating agent; and administering the dosage of the proteinaceous chelating agent to the pregnant human.

In still another aspect, the invention is a method of determining a cause of a birth defect, miscarriage, infertility and childhood neurological dysfunction including delivering an infant from a human female; administering chelating agents to the human female; collecting a urine sample from the human female; and analyzing the urine sample for the presence of heavy metals.

In yet another aspect, the invention is a method of reducing an amount of a heavy metal in a pregnant human including the steps of diagnosing the presence of subclinical levels of the heavy metal in the pregnant human; calculating a suitable dosage of a synthetic chelating agent; and administering the dosage of the synthetic chelating agent to the pregnant human.

Further areas of applicability of the present invention will become apparent from the detailed description provided hereinafter. For example, while the chelation therapies described herein are for mothers, it should be appreciated that chelation therapy may also be used to diagnose metal toxins in men and detoxify these men prior to their impregnation of their respective partners. It should be understood that the detailed description and specific examples, while indicating the preferred embodiment of the invention, are intended for purposes of illustration only and are not intended to limit the scope of the invention.

DETAILED DESCRIPTION OF THE INVENTION

The invention contemplates various well known routes of administration for the chelating agents; these include intravenous bolus, intramuscular bolus, transdermal application and oral administration. DMPS would be most preferably administered transdermally, orally, or intravenously (IV). DMSA would be administered transdermally, or orally. EDTA is contemplated to be administered orally and intravenously. Penicillamine is contemplated to be administered orally. EDTA is contemplated to be administered orally.

Lactate is contemplated to be administered intravenously. Proteinaceous chelators are contemplated to be administered orally, transdermally or intravenously.

Metals contemplated by the invention as targets for chelation therapy include but are not limited to di- and trivalent metal cations, lead, mercury, cadmium, aluminum, cobalt, gallium, lithium, arsenic, beryllium, copper, manganese, nickel, and vanadium. The specificity profiles for the various known chelating agents are well known by the skilled artisan.

The invention contemplates the use of well known chemical chelating agents, both organic and inorganic, in fertile women, including pregnant women. Chemical chelating agents contemplated by this invention for use with the disclosed methods include chelators of divalent and trivalent cations, including synthetic agents such as Ethylenediamine Tetra-acetic Acid (EDTA), British Anti-Lewisite (BAL), Dimercaptosuccinic Acid (DMSA), Dimercaptopropanesulfonic Acid (DMPS), Cyclohexanediaminetetraacetic Acid (CDTA), Diethylenetriaminepenta-acetic Acid (DTPA), Dipicolinic Acid &/or D-Penicillamine (DPA), N-Acetyl-Cysteine (NAC), Dihydroxy-benzene Disulfonic Acid (TIRON), Deferoxamine (DFO), and Triethylenetetramine (TRIEN), as well as substances such as ampicillin, lactate, penicillamine, desferroxamine, Vitamin C, pyruvate, porphyrins, purines, pyrimidines, RNA, DNA, amino acids, and crown ethers.

Similarly, this invention contemplates the use of proteinaceous chelating agents. Examples of proteinaceous chelating agents contemplated by this invention include transferrin, ferritin, metallothionine, albumin, heparin, and synthetically designed proteins engineered for specific binding coefficients, metal specificity, and excretability in the feces.

Chelation agents must be administered to the patient at the proper dosage so as not to induce mineral deficiencies. EDTA should be administered at a dosage of about 1.5 g-3 g per day or about 42 mg/kg of maternal body weight. DMSA should be administered at about 10 mg/kg/day.

EDTA is contemplated to be administered in dosages in the range of 0.21-430 mg/kg/day, and more particularly in the range of 21-43 mg/kg/day. DMSA is contemplated to be administered in dosages in the range of 0.1-100 mg/kg/day, and more particularly in the range of 5-15 mg/kg/day and most particularly in a dosage of 10 mg/kg/day. One DMSA cycle is 3 days on, 11 days off. Alternatively, DMSA could be administered at 5 to 10 day cycles if administered early in pregnancy. DMPS is contemplated to be administered in dosages of 0.5-10 mg/kg, up to 2-3 days/week, assessing the urine samples after every fifth to tenth challenge, or when reaching a decision point in therapy, i.e. attempting to achieve pregnancy.

When chelating agents are used in a preconceptional female, they may be used either with family planning or without family planning With family planning, they may be used from daily to biweekly. When chelating agents are used in the female who is trying to achieve pregnancy, they are ideally limited to a period of infertility at the beginning of the cycle. This period of infertility begins with the onset of heavy or moderate bleeding, denoting a normal menstrual period. The period ends with the onset of fertile mucus, at approximately the $8^{th}$ to the $11^{th}$ day of the menstrual cycle.

By a "fertile human female" what is meant is a woman who is capable of conceiving children or who is pregnant.

The terms "diagnostic provocation" and "chelation-provoked urine tests" and related terms refer to a procedure whereby the patient is administered one of more dosages of chelators, after which the patient's urine is collected for a defined period of time. The collected urine is analyzed for metal content, the metal having been removed from the patient's body by the chelators. The results of this procedure can indicate which metals are present in the patient's body and the approximate levels of the metals, which is subsequently used in designing a course of chelation therapy.

In addition to the above-mentioned 'diagnostic provocation' method of diagnosing the presence of metals in a patient's body, other such diagnostic methods include urinary analysis (without prior provocation with chelators), blood testing, red blood cell analysis, and hair analysis and use corresponding specimens.

Besides mercury and lead, other potentially toxic metals that may be susceptible to chelation treatment include cadmium, arsenic, aluminum, antimony, uranium, and thorium. In addition many of these metals can have synergistic effects when more than one is present in the patient's body, such as the combination of mercury and lead.

The range of normal lab values for toxic metals is the subject of some debate. The metals may be measured with or without prior chelation provocation. The standard values accepted by medical laboratories are measured without chelation provocation. Treatment with chelation medication mobilizes metal stores within in the body to be detected in the urine, thus values obtained post-provocation will be increased. The difference between pre- and post-provocation is also of value in that it reveals the degree of metal toxin burden in the body. It should also be noted that all values used by medical laboratories refer to adult patients. There is currently no level of metal toxins known to be safe for the developing fetus; i.e. the normal value is 0.00 mcg/g (micrograms/gram of creatinine).

Table I below lists a number of metal toxins with the accepted upper limit of normal, acceptable levels (i.e. "subclinical" levels), expressed as micrograms per gram of creatinine (mcg/g) as measured in a urine sample. Subclinical levels of metals are those at or below which immediate medical attention is not considered to be necessary, i.e. there is not thought to be acute toxicity associated with these levels or below, but above which immediate medical treatment including possible chelation therapy may be undertaken.

TABLE I

| | |
|---|---|
| Aluminum | <22 mcg/g |
| Antimony | 0.14 mcg/g |
| Barium | 7.88 mcg/g |
| Bismuth | 0.76 mcg/g |
| Boron | 5.7 mcg/g |
| Cadmium | 0.64 mcg/g |
| Cesium | 10.5 mcg/g |
| Gadolinium | 0.02 mcg/g |
| Gallium | 0.028 mcg/g |
| Lead | 1.4 mcg/g |
| Mercury | 2.14 mcg/g |
| Molybdenum | 0.18 mcg/g |
| Nickel | 9.5 mcg/g |
| Palladium | controversial |
| Platinum | 0.033 mcg/g |
| Rubidium | 2.263 mcg/g |
| Selenium | 0.35 mcg/g |
| Thallium | 0.298 mcg/g |
| Thorium | 0.124 mcg/g |
| Tin | 2.04 mcg/g |
| Tungsten | 0.211 mcg/g |
| Uranium | 0.026 mcg/g |

Table II is similar to Table I, but it lists toxic elements in volumetric concentrations as measured over a twenty-four (24) hour period (micrograms/24 hours, i.e., mcg/24 hr).

TABLE II

| | |
|---|---|
| Aluminum | 25.2 mcg/24 hr |
| Antimony | 0.144 mcg/24 hr |
| Arsenic | 49 mcg/24 hr |
| Barium | 5.5 mcg/24 hr |
| Bismuth | 0.70 mcg/24 hr |
| Cadmium | 0.63 mcg/24 hr |
| Cesium | 10.1 mcg/24 hr |
| Gadolinium | 0.019 mcg/24 hr |
| Gallium | 0.031 mcg/24 hr |
| Lead | 1.5 mcg/24 hr |
| Mercury | 2.17 mcg/24 hr |
| Nickel | 4.41 mcg/24 hr |
| Niobium | 0.086 mcg/24 hr |
| Platinum | 0.038 mcg/24 hr |
| Rubidium | 2.486 mcg/24 hr |
| Thallium | 0.273 mcg/24 hr |
| Thorium | 0.108 mcg/24 hr |
| Tin | 2.25 mcg/24 hr |
| Tungsten | 0.264 mcg/24 hr |
| Uranium | 0.027 mcg/24 hr |

Chelation therapy should proceed via the procedures outlined above until the metal levels are within the normal limits listed above. It will be appreciated that as the dangerous effects of these toxins are further realized, the limits that are considered normal will be expected to decrease over time. For example, some of the actual examples discussed below were begun when the normal limit of mercury was more than twice the limit listed above.

To avoid side effects that might arise from the chelators depleting essential minerals from the patient's body, chelators are generally co-administered with mineral supplements, such as zinc.

PROPHETIC EXAMPLES

Example 1: Chelation in the Gravid Female with Sub-Clinically Materna-Toxic Levels of Lead, Mercury, Aluminum, or Antimony for the Benefit of the Conceptus In this embodiment, a pregnant female would present to the health care worker to be diagnosed for the presence of sub clinically toxic levels of metals. The mother would be given a provocative challenge test using one or more well known chelating agents like for example EDTA. Assuming the mother's levels of toxic metals were shown not to be acutely hazardous to the mother and merely within the subclinical range such as shown in Table I, the pregnant female would then be a candidate for maternal chelation therapy. For example, if the level of a particular metal as measured in the mother's urine is at or above the 'acceptable' levels shown in Table I above, then the mother would be a candidate for maternal chelation therapy. The levels of a particular metal in a mother's body that are considered to be 'subclinical' for the mother might nonetheless be harmful for a developing fetus.

The weight of the mother would be determined. The weight of the mother would then be used to determine the dosage of chelation agents using the dosage information provided hereinabove. The chelating agent would be provided on alternating days with mineral supplementation. The dosage of EDTA for a prototypical 70 kg pregnant female would be preferably in the range of 21-43 mg/kg/day. The chelation dosing would continue for a period of days to weeks. Another factor in calculating the chelator dosages may be based on the gestational age of the fetus. For example, in the first trimester, one half of the typical adult dosage could be used, while 70% of the typical adult dosage could be used in the second trimester, and 90% of the typical adult dosage could be used in the third trimester. Once the levels of lead, mercury, aluminum or antimony reached acceptable (preferably undetectable) levels, the chelation regimen would be altered from a detoxification regimen to a maintenance regimen. This maintenance regimen would continue until birth and beyond. A maintenance regimen would consist of chelation therapy during the first 3-8 days of each menstrual cycle, continuing until pregnancy is achieved, using dosages as described above.

Example 2: Co-Administration of Chelating Agents with Mineral Supplementation or Administration of Chelating Agents Bound to Normal Minerals to Forestall Birth Defects Due to Chelation Therapy In this embodiment, a pregnant female would present to the health care worker to be diagnosed for the presence of sub clinically toxic levels of metals. The mother would be given a provocative challenge test using one or more well known chelating agents, for example EDTA. Assuming the mother's levels of toxic metals were shown not to be acutely hazardous to the health of the mother, the pregnant female may still be a candidate for maternal chelation therapy for the benefit of the baby. In comparison, prior art chelation treatments for pregnant females have been limited to those situations where the mother is so toxic that she must be treated regardless of any concern for the baby.

DMSA would be co-administered with zinc to the gravid female. DMSA would thus bind or chelate zinc in the stomach and then be absorbed in the blood stream. Upon entering the gravid females system, the DMSA would exchange the bound zinc for toxic metals and would then be excreted. Because chelation therapy with DMSA alone might deplete zinc levels in the absence of mineral supplementation, zinc deficiency and its teratogenic effects would be avoided. The use of a chelating agent to enhance absorption of essential minerals on the way in, and thereby to pick up and excrete heavy metal toxins on the way out, may be called "boomerang" chelation. Boomerang chelation could be performed as follows. The chelating agent is administered orally with essential minerals, especially these weakly bond by chelator. Since there will be a high concentration of weakly bond minerals in the stomach, these will be absorbed due to mass action. Once absorbed, the chelator will find more preferred cations, especially strongly bound metal toxins. In the urine, it will be bound in the toxins. By transporting nutrient minerals in, the teratogenic effect of the chelator may be defeated.

The weight of the mother would be determined. The weight of the mother would then be used to determine the dosage of chelation agent and the mineral supplement to be co-administered using the dosage information provided hereinabove. The chelating agent would be provided on alternating days with mineral supplementation provided every day during the pregnancy.

The dosage of EDTA for a prototypical 70 kg pregnant female would be preferably in the range of 21-43 mg/kg/day. The chelation dosing would continue for a period of days to weeks. Once the levels of lead, mercury, aluminum or antimony reached acceptable (preferably undetectable) levels, the chelation regimen would be altered from a detoxification regimen to a maintenance regimen. This maintenance regiment would continue until birth and beyond.

Example 3: Maternal Diagnostic Chelation of the Post-Partum Human Female and Neonate for the Purpose of Determining the Cause of Birth Defects, Still Birth, Miscarriage, Fetal Distress or Other Neurological Impairment A child is born with one or more birth defects. The parents would like to know the cause. A foley catheter is inserted into the mother's bladder to drain and collect the urine. A series of three diagnostic challenges are administered, in each case followed by a six hour collection of urine. In the first challenge 3 grams of calcium EDTA is given in 100 cc of NS over 30 minutes by intravenous piggyback. The urine is collected over six (6) hours beginning with the administration of the drug. A similar provocation is done using DMPS. A dosage of 200-300 mg of DMPS is given via either an oral or intravenous route followed by a six (6) hour collection. Since the mother weighs 175 lbs and DMSA comes in 250 mg capsules, the mother is given 4×250=1000 mg of DMSA orally, again followed by a six hour collection. These provocations revealed substantially elevated levels of lead, mercury, and cadmium. Each of these can cause birth defects in their own right. Each has a synergistic interaction with the others which greatly increases the toxicity. The presence of these toxic metals explains the observed birth defects.

Example 4: Maternal Chelation in the Lactating Female for the Benefit of the Suckling Newborn Toxic heavy metals can be transferred to the neonate across the breast-milk just as they are transferred across the placenta. To protect the fetus from accumulating toxic metals an alternate route of excretion should be provided. If some of the toxic metals in the blood are excreted into the maternal gut or maternal urine then less is available to be excreted via the breastmilk, and thus to the infant. Excretion into the gut is favored by the presence of binding agents, including: activated charcoal, cilantro, *chlorella*, ETDA (which is minimally absorbed from the gut) and garlic or other herbs with the high sulfhydryl content. Also, increased bowel motility favors gut excretion. Any factor which increases bowel motility will favor excretion. Vitamin C is useful in this regard.

Urinary excretion is favored by fluid administration, either orally or intravenously. Alkalinizing the blood favors excretion of metals from tissue into the blood. Alkalinizing maternal urine may favor excretion of metals from the blood into the urine. Oral administration of antacids allows acid to be excreted from the blood into the gut where it is neutralized. Thus, the mother is given oral EDTA, garlic, and activated charcoal as well as oral antacids. With these protections the toxin excretion is favored and redistribution to unintended targets is minimized.

The mother could be treated first with a series of DMSA treatments, mobilizing lead into the urine. Only a small amount of DMSA is used and DMSA is readily excreted into the urine. This lowers the lead content—and since lead makes other metals more toxic, this will not only reduce the amount of lead reaching the fetus, but also reduce the toxicity of any other metals reaching the fetus. The toxicity of DMSA is reduced by co-administration of zinc. Oral methionine can be used to prevent DMPS from crossing membranes. After several treatment cycles with DMSA, DMPS is used to root out mercury, the second most toxic metal after palladium.

The maternal chelation treatments can be done one day per week. The chelating agents will generally be cleared from the maternal blood in two to six (2-6) hours. The infant can consume stored milk during this time period and after the chelating agent has passed into the maternal urine the infant can return to breastfeeding. One to two days later the maternal red blood cells can be checked for toxic metals. If the chelation therapy is successful then the red blood cells with be depleted of toxic metals as these toxins were excreted into the urine and gut. Since the red blood cells are the source of heavy metals for the infant, reduction in heavy metals in the maternal RBCs will suggest that the chelation therapy is successful in protecting the infant from heavy metal transfer.

Example 5: Maternal Chelation in Women with Multiple Previous Spontaneous Abortions The patient is given a chelation-provoked urine test that diagnoses lead toxicity. For the test, the woman is administered a protocol of oral DMSA 250 mg once by mouth three times a day, and her urine is collected over a period of twenty-four (24) hours. The test results indicate that her body contained a store of lead.

After this diagnostic chelation, she is given a therapeutic chelation treatment with three capsules of DMSA three times a day for three days a week. Each three-day cycle constitutes one cycle of treatment, and the patient typically receives fifteen (15) cycles of treatment. A subsequent chelation-provoked urine test reveals a decrease in total body lead. The patient stops her chelation treatments and prepares to achieve pregnancy. She would be expected to achieve pregnancy and, subsequently, deliver a healthy baby at term.

Example 6: The First Time Mother Presenting with Spontaneous Abortion and Vaginal Bleeding, and a Positive Pregnancy Test A patient might present with vaginal bleeding, a positive pregnancy test, and a recent spontaneous abortion. The patient would be given a diagnostic oral provocation chelation. Oral provocation would be given by DMSA 250 mg once by mouth three times a day. During the provocation her urine would be collected for 24 hours.

The diagnostic provocation would reveal a store of lead and tin in her body. Subsequently, she would be given oral DMSA with fifteen cycles of treatment. Having completed her DMSA treatment she is now ready to achieve pregnancy, but will continue chelation treatments because she will not have removed all of the lead. She continues chelation treatments in a manner which is coordinated with the menstrual cycle. She does this by beginning chelation in each cycle with the onset of heavy or moderate bleeding, which would indicate the beginning of a new cycle. She continues the chelation treatments until she detects fertile mucous at her entroitus, indicating the onset of the fertile period. Alternatively, she could stop after eight (8) days of chelation treatment. By either of these two methods she restricts her chelation treatment to the early part of her cycle, when she is not fertile. She, subsequently, would became pregnant and not miscarry. She would also be given oral EDTA as a chelation treatment during pregnancy. At the conclusion of the pregnancy, she would deliver a healthy child.

Example 7: The Mother Presenting with a Previous Child with Attention Deficit Disorder This patient would present with a previous child with attention deficit disorder, behavioral problems, autism spectrum disorder and poor language development. The mother-patient might be diagnosed as having elevated levels of mercury using hair analysis or other suitable diagnostic methods. She would be given oral DMPS 300 mg once a week. At the conclusion of the pregnancy, her subsequent child would not have attention deficit disorder.

Example 8: The Lactating Mother with High Lead and Mercury

This patient may have experienced three recurrent spontaneous abortions. She would be given an intravenous injection of DMPS as a diagnostic provocation. Her diagnostic provocation would reveal that she had lead and mercury.

It is well known that lead and mercury are transferred to the infant through the breast milk. In order to prevent the lead and mercury from transferring into the breast milk, oral therapeutic chelation of the mother would be performed by both oral EDTA and oral DMPS. The oral chelating agents being poorly absorbed in the human alimentary canal, tend to remain in the gut. As a result, lead and mercury are attracted to the gut and excreted in the feces and, therefore, less lead and mercury get transferred to the child through the breast milk.

Example 9: Gestational Chelation

In this case, a woman could be a 35-year-old gravida 4, para 3, who presents with a history of three previous children with autism. She is now pregnant with the fourth. She wonders if anything can be done to prevent autism in the fourth child. The first set of treatments involves binding the metal toxins in the gut. She is given oral EDTA, which remains in the gut, and oral garlic. During chelation treatments, she is also given activated charcoal oil orally, which binds the mobilized toxins in the gut. When she gets the chelation treatments, she also takes oral antacids to lower her systemic PH so that metal toxins are freer to leave the cells. She is placed on a program of oral vitamin C and oral selenium. The oral vitamin C augments her own natural ability to make glutathione. She also takes L-Cysteine and N-Acetyl-Cysteine which also augment the natural ability to make glutathione. She takes oral selenium which binds the heavy metals and takes them out of solution by forming irreversible, tight heavy metal selenites which are unsoluble and effectively bind the heavy metals so that they cannot do any harm.

Chelation therapy preferably begins with the water soluble chelating agent EDTA because EDTA does not cross membranes well. The urine, which is collected after EDTA is analyzed for beneficial mineral nutrients, such as copper, zinc, manganese, et cetera, and chromium and whatever beneficial nutrients have been removed by the EDTA are replaced orally. After the EDTA has been used to lower lead concentration, antibiotics can also be used as chelators.

Next, the patient is given oral DMSA with zinc. Oral DMSA with zinc allows the oral DMSA to be used as a zinc chelator as it goes from the stomach to the blood stream bringing zinc into the body. Once in the body, it picks up lead, mercury and other heavy metal toxins and is excreted in the urine, thus this demonstrates the principle of boomerang chelation in which the chelating agent is used to bring in a nutrient before removing a toxin. As discussed above, the principles of boomerang chelation are that the patient is given a high oral concentration of a nutrient mineral which is weakly chelated, along with the chelator. Due to mass action, chelator transports the mineral across the gut into the body. Once in the body, the chelator picks up a toxin for which it has stronger affinity, this usually being something more toxic, such as lead or mercury. This minimizes the harmful effects of the chelating agents.

Next, a DMPS may be used. DMPS has very high affinity for mercury, which is the second most toxic metal. Since mercury is the second most toxic metal, excretion of mercury is a high priority. Absorption of mercury by either the brain or the fetus can be blocked by a concurrent administration of methianine. Thus, a protein meal or oral methianine are used before DMPS and these then block the DMPS from getting into either the brain or the baby. Then the DMPS can be given orally and it causes urinary excretion of the mercury.

Finally, lipoic acid can be used. Lipoic acid crosses membranes easily and, therefore, a different principle is used with lipoic acid. There is a small amount of lipoic acid placed in the amniotic cavity. It will be absorbed by the baby. Lipoic acid can then act as a chelator, starting in the baby's compartment and diffusing out into the maternal compartment. Since the maternal compartment is much larger, there will be a drop in the toxins within the baby, as these toxins get redistributed into the larger maternal compartment. This method of chelation will work best if the mother is previously depleted of toxic metals so that lipoic acid could not carry a toxin from baby into mother and then pick up another toxin in the mother and bring it back into the baby. So this is why the preparation is done with water soluble chelators which would not cross membranes. These would deplete the blood vessels and the body of toxins, so that when chelators, such as lipoic acid is given, it will cause a net movement of toxins from the baby into the mother because there are more open toxin binding sites since the mother has been depleted of metal toxins.

In a pregnancy provocation, a number of things need to be demonstrated. The most important thing that needs to be demonstrated is that when the chelator is given, that there is not redistribution of toxins from the mother into the baby. Thus, the three tests of monitoring are used. One is amniotic fluid; any metal; second is red blood cell heavy metals; and third is maternal urine heavy metals and the fourth is maternal gut heavy metals. The goal of a successful chelation treatment would be to deplete the red cells of heavy metal toxins such that the toxins are either excreted in the urine or excreted in the gut without significant transfer to the baby. This can be facilitated by placing in the gut, nonabsorbable chelators, such as oral EDTA and oral garlic. The pregnancy chelation is obtained in maternal urine, maternal feces, maternal red blood cells and amniotic fluid or fetal urine. Then, the chelatoring agent is given to the mother. This could be calcium EDTA, intravenous or oral DMPS or oral DMSA. If significant amounts of oral binders are given, much of the mobilized metal toxins will become bound in the gut and excreted. If vigorous hydration is given either oral or intravenously, then what does not get bound in the gut will tend to be excreted in the urine, since urine can constantly flow out of the maternal kidneys, whereas the fetal amniotic fluid is a closed compartment. A very small catheter can be placed in the fetal compartment by placing a small epidural or spinal needle into the amniotic cavity and then passing an epidural catheter through such a needle Amniotic fluid then can be sampled before and after chelation treatment to determine whether there is a movement of metal toxins from mother into baby after maternal chelation.

If there is no significant mobilization of metal toxins from mother into baby during the diagnostic chelation, then the mother can be successfully depleted of heavy metal toxins while at the same time replenished with beneficial mineral nutrients. Over time, the mother will then become relatively clean of toxins comparted to what she started and compared to the baby. Most of the metal toxins bio concentrate into the fetus at levels 200% to 800% of what they are in the mother, so in general, the chelator which could mobilize toxins across the placenta should be likely to mobilize them in the direction from baby to mother, since toxins are concentrated in the baby relative to the concentrations in the mother. After a period of EDTA chelations have been given, the mother will be relatively depleted of lead and other heavy metal toxins. This can be followed by a period of treatment with oral DMSA combined with zinc. The oral DMSA with zinc will result in boomerang chelation transporting zinc and lead out. Again, a diagnostic chelation needs to be done to verify that there is no significant transport of toxins from mother into baby.

Finally, DMPS can be used and again, a diagnostic chelation is done as described above, to demonstrate that the DMPS does not mobilize toxins from mother into baby. Separation with oral methianine is given to block transport of toxins into the baby. After the mother has been treated with one or more of the above chelators, the mother is relatively depleted of metal toxins. During the normal course of pregnancy, toxins bio-concentrate from the mother into the baby so the normal baby will have higher concentration of toxins than the mother originally had in her system. Finally, lipoic acid is given. The maximum safety would result from doing lipoic acid through the epidural catheter. This would mean that a small amount of lipoic acid is given in a small volume of amniotic fluid and then picks up toxins there, diffuses across the placenta and into the larger, much larger maternal volume of distribution so that there will net export of toxins from the baby into the mother.

If it is relatively certain that the mother has been depleted of toxins, she can take oral lipoic acid which will also result in redistribution of toxins from the higher concentration found in the baby to lower concentration found in the mother.

Before provocation and after provocation monitoring of maternal red blood cell elements can also demonstrate a beneficial effect of chelation. The heavy metal toxins that the baby is exposed to are those carried on maternal serum proteins and maternal blood cells, especially the red blood cells. Before and after chelation should demonstrate that the red blood cells are depleted of heavy metal toxins, and thus the amount of heavy metal toxins the baby is exposed to should be decreased. However, one has to recall that the red blood cells can either accept heavy metal toxins from maternal tissues or baby tissues, or disseminate heavy metal toxins either through maternal tissues or from baby tissues.

Finally, methods of chelation treatments can be used in the mother which merely augment her normal processes. Specifically, this could be either high dose vitamin C, which would augment production of glutathione and, therefore, would cause excretion of heavy metals into the gut. If these heavy metals are bound in the gut by chelators which are bound in the gut, then the natural chelation mechanism will work to deplete the maternal system and maternal red blood cells of heavy metal toxins. Thus, the baby will be exposed to less toxins. Another benefit of glutathione is that glutathione is a detoxifier of many other metal toxins, such as pesticides. Thus, the availability of glutathione will detoxify many other toxins. Glutathione could be done in addition to intravenous vitamin C. Intravenous vitamin C also detoxifies not only heavy metal toxins, but many other toxins, including pesticides. Thus, either intravenous vitamin C or intravenous glutathione or both in combination would be a general detoxification treatment, which would cause elimination of heavy metal toxins, organic chemical and pesticide toxins.

Actual Cases:

Case No. 1: The patient had multiple previous spontaneous abortions. She received a chelation-provoked urine that was used to diagnose lead toxicity. This was done by taking a protocol of oral DMSA 250 mg once by mouth three times a day. She collected her urine for 24 hours. The resultant test indicated that her body contained a store of lead; on provocation, her urinary lead concentration was 20 mcg/g creatinine. After this diagnostic chelation, she was given therapeutic chelation with DMSA three capsules three times a day for three days a week. Each three-day cycle would constitute one cycle of treatment. This patient received 15 cycles of treatment which would be typical. A follow-up chelation-provoked urine revealed a decrease in total body lead. She then stopped her chelation and prepared to achieve pregnancy. She achieved pregnancy and, subsequently, delivered a healthy baby at tem'.

Case No. 2: The patient presented with vaginal bleeding and a positive pregnancy test. She had a spontaneous abortion and, subsequently, was tested by oral provocation. Oral chelation provocation was given by DMSA 250 mg once by mouth three times a day. During the provocation her urine was collected for 24 hours. The diagnostic provocation revealed a store of lead and tin in her body; the urinary lead concentration after provocation was 14 mcg/g creatinine, and the tin was 9 mcg/g creatinine. Subsequently, she was given oral DMSA with five cycles of treatment. She, subsequently, became pregnant and did not miscarry. She was also given oral EDTA during pregnancy. At the conclusion of the pregnancy she delivered a healthy child.

Case No. 3: The patient had a previous child with attention deficit disorder, behavioral problems, autism spectrum disorder and poor language development. The patient was diagnosed as having mercury by the use of a hair analysis; mercury was 1.5 mcg/g hair. She was given 500 mg of oral NAC per day throughout the pregnancy. The NAC promotes the formation of glutathionine, which is the body's natural chelating agent. She was also given vitamin C and selenium. At the conclusion of the pregnancy, her subsequent child did not have attention deficit disorder.

Case No. 4: The following illustrates the use of preconceptional chelation as a treatment for infertility and also prevention of miscarriage. The patient was a 33-year-old G4P2022 who was infertile with two previous miscarriages. She had a chelation provocation using four (4) capsules of DMSA 250 mg followed by a six (6) hour urine collection. There was also an initial unprovoked urine collection. The unprovoked lead was 0 mcg/g creatinine and the provoked lead of 13.6 mcg/g creatinine. The unprovoked cadmium was 0.73 mcg/g creatinine and the provoked cadmium was 1.79 mcg/g creatinine. The unprovoked tin 2.5 mcg/g creatinine and the provoked was 12.5 mcg/g creatinine. The patient underwent four (4) months of treatment with oral DMSA. She received four (4) capsules of DMSA (250 mg capsules) three (3) times daily and three (3) days per week followed by a four (4) day rest period. After the four (4) month treatment she had a follow up provocation. The lead was down to 1.34 mcg/g creatinine from previous level of 13.6 mcg/g creatinine. The cadmium was down to 0.18 mcg/g creatinine from previous 1.79 mcg/g creatinine. The tin was 0.9 mcg/g creatinine down from previous 12.5 mcg/g creatinine. During the treatment her energy level improved and her chronic fatigue resolved. She had a successful term pregnancy. This case illustrates chelation to treat infertility and prevent miscarriage.

Case No. 5: The patient is a 27-year-old G0P0 with irregular menstrual cycles and chronic fatigue, but her chief complaint was infertility. A DMPS chelation provocation was performed which revealed (all values in mcg/g creatinine):

| Lead | 6.39 (normal <1.41) |
|---|---|
| Antimomy | 0.84 (normal <0.14) |
| Mercury | 38.55 (normal <6.97) |

She also had an EDTA provocation (in mcg/g creatinine):

| Lead | 25.14 (normal <1.41) |
|---|---|
| Aluminum | 176.8 (normal <98.7) |
| Cadmium | 3.18 (normal <0.76) |
| Nickel | 36.9 (normal <9.5) |
| Uranium | 0.33 (normal <0.013) |

She then had a laser laparoscopy for endometriosis and soon became pregnant. She subsequently miscarried at fourteen (14) weeks. After the miscarriage, she had chelation treatments. This consisted of 3 grams of calcium EDTA and 3 grams of vitamin C intravenous push two (2) times per week. She also had DMSA 500 mg per day orally. After a period of time she had repeat diagnostic provocations to determine readiness for pregnancy. On the repeat EDTA provocation her lead had previously been eighteen times (18×) normal and now was down to eight times (8×) noinial. The aluminum was previously two times (2×) normal, now down to two tenths of (0.2×) normal. The nickel was previously four times (4×) normal, now down to three (3×) normal. On the repeat DMPS provocation her lead was previously four times (4×) normal, now down to normal. Mercury was previously five times (5×) normal, now down to normal. Antimony was previously six times (6×) normal, now down to one and one half times (1.5×) normal. The patient's chronic fatigue improved. She subsequently achieved pregnancy and delivered a healthy baby at tenth After the birth the baby was standing at two (2) months of age and displayed above average neurological development. This case illustrates prevention of miscarriage by chelation and exemplary neurologic development in a child whose mother was previously known to have multiple neurotoxins.

Case No. 6: The patient came to labor and delivery after a relatively uneventful pregnancy. After the patient came to labor and delivery, the mother was placed on the fetal heart rate monitor. The monitor did not show any evidence of decelerations that would be indicative of danger, however, the tracing also did not show any acceleration that would be indicative of safety. After several hours, the patient had a sudden bradycardia indicative of a sudden fetal distress in the baby. Since obstetric staff had been present in labor and delivery, an immediate cesarean section was performed with the baby delivered in sixteen (16) minutes, a very rapid response time. Despite the outstanding obstetrical care given in this case, the infant suffered very severe brain damage and was finally taken off the respirator and allowed to die several months after birth. Three days after delivery, the mother was given an oral DMSA diagnostic provocative chelation challenge. The results of this test, a chelation-provoked urine test, revealed the presence of both lead and mercury. Both lead and mercury impair the function of the Krebs' cycle which is the main power generating and energy generating biochemical mechanism of the cell. There were other vitamin deficiencies that exacerbated the problems associated with lead and mercury. In addition, both lead and mercury generate free radicals. Much of the brain damage that occurs during fetal distress, or for that matter with adult stroke or other ischemic scenarios, occurs after the event; this is the mechanism of ischemia-reperfusion. In the ischemia-reperfusion period brain damage increases because of (1) energy failure, (2) free radical stress and (3) glutamate release. Glutamate release is increased because of the mercury that increased the presence of glutamate. Glutamate is the main excitotoxic neurotransmitter of the brain. When large amounts of glutamate are released, they overstimulate the already energy-depleted cells and cause further damage in a feed-forward mechanism. Therefore, the presence of mercury increased the glutamate and caused increased brain damage. In addition, both lead and mercury cause the production of free radicals which increases tissue damage. In addition, both lead and mercury block pyruvate dehydrogenase. This enzyme is the gateway for energy stores coming into the cell. Blockage of pyruvate dehydrogenase results in severe compromise of the cell's energy producing capacity.

The use of the chelation-provoked urine test in this case demonstrates that the causes of the fetal impairment, specifically, lead and mercury, which have nothing to do with obstetric care. This may be beneficial in malpractice litigation to prevent unfair blaming of the physician when, in fact, another cause (namely, lead and mercury) may actually the cause of the brain damage. In this case, the plaintiff's attorney settled for a nominal amount ($50,000) when he realized he could not suppress the results of the chelation provoked urine test or exclude it from the case. Accordingly, it is within the scope of the present invention to prepare a report on the test results and introduce the results of the chelation diagnostic tests in such a malpractice case.

Case No. 7: Similar to Case No. 6 presented above, the patient came to labor and delivery with a relatively normal tracing and even had numerous accelerations. There was the sudden reduction in the fetal heart rate, known as a bradycardia. This was a sign of fetal distress. Because obstetricians were standing by, the baby was delivered in 12 minutes, a remarkably rapid response time. Despite the rapid response, the baby still suffered hypoxic ischemic encephalopathy that resulted from fetal distress. This patient had oral provocative DMSA challenges with one 250-mg capsule of DMSA followed by a six (6) hour urine collection. The results of this provocation are as follows (all values in mcg/g creatinine):

| lead | 4.79 (normal <1.41) |
|---|---|
| nickel | 77 (normal <9.5) |
| tungsten | 6.41 (normal <0.34) |
| uranium | 0.05 (normal <0.031) |

The patient also had a DMPS provocation. The challenge was one 300-mg capsule of DMPS followed by a six (6) hour urine collection. The results were as follows:

| | |
|---|---|
| lead | 4.6 (normal <1.41) |
| nickel | 132 (normal <9.5) |
| tungsten | 7.07 (normal <0.34) |
| uranium | 0.034 (normal <0.013) |

These provocations reveal the presence of toxic metals, which could exonerate the physician in the event of a lawsuit, or even better discourage the plaintiffs' attorney from filing a lawsuit. No lawsuit was filed in this case.

Case No. 8: In another case, a mother was known to have lead and mercury because she had diagnostic provocation before pregnancy. She was given oral EDTA 3000 mg per day, vitamin C 5000 mg per day, selenium 200 micrograms three (3) times per day, and garlic 6000 mg per day. At the time of delivery, she had a normal delivery with no evidence of fetal distress. In this case, oral EDTA limited the fetal exposure to maternal lead which is usually substantial in pregnancies. This fetus was enabled to have a normal pregnancy and delivery because of the oral chelation treatment. Subsequent to the delivery, the child was healthy and neurologically normal.

Case No. 9: The patient was a 23-year-old G-4, P-3003 who had been admitted with pain secondary to preterm labor. The gestational age was 27 weeks by early ultrasound, but 24 weeks by fetal size. The patient had intermittent variable fetal heart rate decelerations. The initial impression was intrauterine growth retardation with preterm labor. Due to recurrent decelerations and severe preeclampsia, the decision was made to proceed with caesarian section. Apgar test scores were 3 at 1 minute, 3 at 5 minutes, 3 at 10 minutes with a birth weight of 631 grams. These Apgar test scores indicate severe hypoxic injury to the newborn.

In the postpartum period, the mother was examined with urine organic acid test. This revealed deficiencies of vitamin B1, B2, B3 and vitamin C. Marked deficiencies were seen of folic acid and B12. An unprovoked assessment of urine toxic metals revealed elevated amounts of tin and uranium, as well as the presence of mercury, antimony and cadmium at approximately the level of the reference range. Provocation with EDTA (3 grams calcium EDTA in 100 cc NS over 30 minutes followed by a 6 hour urine collection which begins with the infusion of the calcium EDTA) lead to significant excretion of lead, mercury, cadmium and uranium. The uranium was more than forty times (40×) the reference range. Provocation with DMSA (1000 mg PO×1 followed by 6 hour urine collection) resulted in excretion of a number of metals, including lead, mercury, cadmium and uranium. Uranium appeared at a level at more than one hundred times (100×) the reference range.

The findings here provide an example of a peripartum tragedy caused by severely elevated levels of maternal heavy metals and deficiencies in folic acid and vitamin B12. The clinical findings in this case could have been influenced and therefore explained by the previously unsuspected presence of toxic metals. These toxic metals have numerous toxic effects, including impairment of the Kreb's cycle, which leads to impaired energy production by the fetus, and thereby contributes to fetal distress. Preconception evaluation of toxic maternal metal levels, vitamin deficiencies and appropriate therapy, including chelation treatment and vitamin supplementation, will avert such complications.

Case No. 10: The patient was a 34-year-old G-3, P-2 at 36 4/7 weeks. The patient had decreased fetal movements for fifteen (15) days with contractions every fifteen (15) minutes. The patient came in with a nonreactive Non-Stress Test (NST) and decreased fetal movements. Past medical history was unremarkable. Pelvic exam revealed a minimally dilated cervix (1 cm dilated, 70% effaced, −2 station).

Fetal evaluation revealed that the health of fetus was in jeopardy. The patient was admitted to the hospital with nonreactive fetal heart rate tracing and minimal variability. Acoustic stimulation was performed and the fetus was unresponsive. The fetus had a period of late decelerations and a positive contraction stress test.

The patient was taken for a primary cesarean section. The initial assessment of the neonate suggested hypoxic depression. The Apgar test scores were 0 at 1 minute, 4 at 5 minutes, 8 at 10 minutes. The respiratory evaluation of the neonate (cord gas) revealed respiratory acidosis (pH 7.16, PCO2 51, PO2 59, bicarb 17, base excess −11). The neonate was found to have hyperphosphatemia, hypomagnesemia, hyperkalemia and constriction of the ductus arteriosis. The mother was also found to have elevated nucleated red blood cells to 130, suggesting long-standing hypoxia with bone marrow response. In summary, the clinical scenario describes a severely sick neonate.

Biochemical evaluation by gas-liquid-chromatography indicated the following:

Chlorinated pesticide evaluation revealed DDT and DDE. Organophophorus pesticides were negative.

Urine organic acid evaluation revealed deficiencies of thiamine, riboflavin, niacin, B12, biotin, folate, manganese, copper, magnesium, vitamin C and lipoic acid. There was disruption of fatty acid oxidation, markedly elevated lactate and pyruvate, with decreases in the other Kreb's cycle intermediates, suggesting that energy metabolites were blocked from entering the Kreb's cycle at pyruvate dehydrogenase.

Evaluation of urine amino acids suggested deficiencies of folate and molybdenum.

Urinary heavy metal testing was as follows: unprovoked urine revealed elevations of lead, mercury, aluminum, antimony, arsenic, barium, gallium, nickel, tin, tungsten and uranium. DMSA challenge (250 mg PO×1 followed by 6 hour urine collection) revealed elevated amounts of lead, aluminum, antimony, barium, nickel, gallium, tin, tungsten, and uranium. DMPS provocation was done with DMPS 300 mg PO×1 followed a 6 hour urine collection. DMPS provocation revealed elevated levels of lead, mercury, aluminum, antimony, cadmium, nickel, tin, tungsten and uranium. In summary, there were numerous biochemical factors which would harmfully influence the baby's energy metabolism. These factors, including nutrient deficiencies and toxic metals, could explain the unfortunate birth outcome.

Case No. 11: The patient was a 26-year-old G-5, P-3013 who had come to the hospital with severe abdominal pain for five (5) hours and bleeding. The baby had bradycardia (slow heart beat) with a heart rate 70-80 bpm. The mother was taken for an emergency Cesarean section. The neonate was born in very poor condition—the Apgar test scores were 0 at 1 minute, 0 at 5 minutes, 2 at 10 and 4 at 20 minutes. A blot clot covering 60% of the placenta indicated abruption.

Urine organic acid analysis revealed deficiencies of B12, riboflavin, vitamin C, and copper. A DMSA provocation was performed by giving 1000 mg DMSA orally ×1 followed by six (6) hour urine collection. DMSA provocation revealed elevated levels of lead, mercury, tin, uranium and tungsten.

An EDTA provocation was performed by intravenously infusing 3 grams of calcium EDTA in 100 cc normal saline over thirty (30) minutes, followed by a six (6) hour urine collection. Results revealed elevated levels of lead, mercury, aluminum, cadmium, gadolinium, gallium, tin, tungsten, and uranium.

This case portrays an alarming scenario in the field of obstetrics. An unknown patient appears at the hospital requiring an emergent Cesarean section, and despite the best efforts of the obstetrician, disaster results. To defend against malpractice litigation, the obstetrician must demonstrate the results were due to a cause other than the treatment provided at the hospital.

In this case, multiple heavy metals were present, as well as nutrient deficiencies. These biochemical factors can explain the poor birth outcome. This gives the obstetrician a defense against an unfair malpractice suit.

Case No. 12: The patient was a 17-year-old G1 P0 at 39 weeks gestational age who presented to the hospital with labor pains. The fetal heart rate tracing revealed worrisome decelerations. Meconium was noted at the time of the delivery. The baby was floppy at birth and had no respirations (Apgar test scores 3 at 1 minute and 6 at 5 minutes). The neonatologist was called to revive the depressed baby. The infant had a poor response to resuscitation. The cord gas evaluation revealed the baby who was acidotic (pH 7.03). The pCO2 was 73 indicating respiratory acidosis. Base excess was −13, indicating metabolic acidosis.

Urine organic acid analysis revealed impaired fatty acid oxidation and deficiencies of carnitine and/or riboflavin. Pyruvate and lactate were both elevated, suggesting impairment of the Kreb's cycle. Urine organic acid assessment indicated deficiencies of vitamin C, vitamin E, vitamins B1, B2, B3, B5, B12, biotin, co-enzyme Q10, carnitine, lipoic acid, magnesium, selenium, manganese, cromium, argentine, and Vanadium.

A DMPS provocation was performed by giving DMPS 300 mg PO×2 followed by a six (6) hour urine collection. Urine element testing revealed marked elevation of nickel as well as abnormally elevation of arsenic, cadmium and lead.

In summary, it is generally thought, in obstetrics, that fetal distress, low Apgar test scores, acidotic cord pH have little do to with cerebral palsy and other neurologic untoward outcomes. This is based on a large quantity of establish science that remain unpersuasive in the court room. It is unpersuasive because the obstetrician is unable to point to an alternative cause for the bad outcome. In this case we see elevation of nickel which toxically impairs the electron transport chain. Cyanide, another electon transport chain toxin, causes biochemical asphyxiation in the presence of normal amounts of oxygen by blocking the beneficial effect of oxygen on the electron transport chain. Lead, cadmium and arsenic can impair the function of pyruvate dehydrogenase. This enzyme is critical to the function of the Kreb's cycle, and its impairment is indicated by the elevation of pyruvate and lactate. The various dysfunctions of the Kreb's cycle and electron transport chain could impair the baby's energy production, i.e. they are not caused by any negligence by the obstetrician, and there is currently no technology in obstetrics that can detect these problems. Thus, the obstetrician can demonstrate that the problems in the baby were not caused by him.

Case No. 13: The patient was a 31-year-old Latin American female G1P0. She presented with a chief complaint of infertility. An EDTA provocation was performed on the woman and her husband. This was done with 3 grams of EDTA and 3 grams of vitamin C intravenous push followed by a six (6) hour collection. Lead was 6.15 mcg/g creatinine (normal<1.41); mercury 3.09 mcg/g creatinine (normal<6.97); cadmium was 0.86 mcg/g creatinine (normal<0.76). The husband's test results were similar.

The woman received ten (10) intravenous EDTA chelations as did the woman's husband. The chelation treatments for both the husband and the wife were done by giving 3 grams of calcium EDTA plus 3 grams of vitamin C intravenous slow push once per week. She delivered a normal healthy baby at term. This child has a large vocabulary relative to his age of 2 years old and seems to have admirable neurological development.

Case No. 14: The patient was a 32-year-old white female, gravida 2, para 2003 who became pregnant after having been successfully treated by an infertility doctor for an ovulatory disorder following a previous pregnancy. She was initially found to have mercury on a hair test and was treated at pregnancy with selenium. She had a second pregnancy and delivered a second healthy infant before having her metals evaluated.

In October of 2003, after the first two pregnancies, the patient had a DMPS provocation which revealed the following results (all values in mcg/g creatinine):

| | |
|---|---|
| lead | 7.9 (normal <1.41) |
| mercury | 7.3 (normal <2.14) |
| antimony | 0.48 (normal <0.14) |
| arsenic | 159 (normal <50) |
| cadmium | 0.82 (normal <0.64) |
| nickel | 9.3 (normal <9.5) |
| thorium | 0 (normal <0.124) |
| tin | 10.4 (normal <2.04) |
| uranium | 0.042 (normal <0.026) |

The patient was treated preconceptually. She had a series of intravenous DMPS chelation treatments from October 2003 to May 2004. After these chelation treatments, the lead was reduced to 0.9 mcg/g creatinine, the mercury to 6 mcg/g creatinine, the antimony down to 0.05 mcg/g creatinine, arsenic of 20 mcg/g creatinine, cadmium of 0.16 mcg/g creatinine, nickel of 3.2 mcg/g creatinine, thorium of 0.019 mcg/g creatinine, tin of 0.4 mcg/g creatinine, and uranium of 0 mcg/g creatinine. She was given oral DMSA and essential daily defense and had a follow up in October 2005 when the lead was 2.6 mcg/g creatinine, the mercury was 4.6 mcg/g creatinine, antimony was 0.18 mcg/g creatinine, arsenic was 34 mcg/g creatinine, cadmium 0.17 mcg/g creatinine, nickel 0.7 mcg/g creatinine, thorium 0 mcg/g creatinine, tin 3.03 mcg/g creatinine, and uranium 3 mcg/g creatinine. This experiment would suggest that the therapeutic benefit was preserved because most of the chelation treatments were over by May 2004 and only a little bit of chelation treatments occurred between May 2004 and October 2005.

During the treatment period, the patient had an intravenous EDTA provocation in January 2004 which revealed a lead of 4.6 mcg/g creatinine, mercury of 0 mcg/g creatinine, antimony of 0.18 mcg/g creatinine, arsenic of 90 mcg/g creatinine, cadmium of 1.59 mcg/g creatinine, nickel 41 mcg/g creatinine, thorium of 0.22 mcg/g creatinine, tin 0.6 mcg/g creatinine. After intravenous EDTA and DMPS chelation treatments, in June 2004, she had lead of 5.5 mcg/g creatinine, mercury 0 mcg/g creatinine, antimony reduced to 0.15 mcg/g creatinine, arsenic reduced to 32 mcg/g creatinine, cadmium was 1.75 mcg/g creatinine, nickel was 30 mcg/g creatinine, thorium 0.06 mcg/g creatinine, tin 0.3 mcg/g creatinine. A little bit of DMSA with essential daily defense and the long-term follow up in October of 2005, was lead of 7.97 mcg/g creatinine, mercury of 9.4 mcg/g creatinine, antimony 0.09 mcg/g creatinine, arsenic 46 mcg/g creatinine, cadmium 2.66 mcg/g creatinine, nickel 26 mcg/g creatinine, thorium 0 mcg/g creatinine, tin 0.4 mcg/g creatinine, and uranium 0.012 mcg/g creatinine.

This case demonstrates the benefit of preconceptual chelation provocation and chelation treatments, and that the benefit can be relatively stable after a thorough series of chelation treatments.

Accordingly, the present invention can prevent birth defects, spontaneous abortions and childhood mental disorders and improve mental development of the fetus, infant and child. Another aspect of this invention is that the person who benefits from the treatment, the child, is different from the person who received the treatment, the mother. Another advantage is that the processes of embryonic and fetal development and infant development, are re-imagined not as inexorable sequences that may result in disaster, but rather physiologic processes that can be remedied when they go awry.

Organ and tissue development occurs as a timed sequence. It only occurs once. If development goes awry, the development cannot be repeated or revised later. Reproductive chelation therapies, including chelation provocation and chelation treatments, enhance the development of the organs and tissues, including the brain.

The new reproductive chelation therapies discussed herein, including chelation provocation and chelation treatments, can diagnose and remove metal toxins preconceptually, i.e. before the pregnancy has even been conceived. This will reduce birth defects, miscarriages, and neural developmental problems without jeopardizing the fetus and/or embryo.

Reproductive chelation treatments can remove metal toxins during pregnancy preventing or limiting the accumulation of toxic metals during brain growth and development. Reproductive chelation evaluations can identify non-obstetric causes of fetal maldevelopment. This fetal diagnostic information can demonstrate that fetal neural developmental catastrophes such as fetal distress and resultant brain damage can be caused by factors unrelated to labor management. This would be helpful in malpractice litigation.

Reproductive chelation therapies can enhance development of the fetus and embryo with resultant better long-term health. This can improve the intelligence of postnatal children and improve their long-term intellectual capacity, emotional development, psychological development and job performance.

Reproductive chelation therapies can improve neurologic development leading to improved postnatal function and better long-term intellectual, behavioral and emotional performance.

Reproductive chelation treatments can remove metal toxins from the offspring so as to allow subsequent healthy development after treatment is over.

Reproductive chelation treatments can be coupled with adjunctive measures, such as co-administration of mineral supplements, so as to prevent the harmful effects of chelation.

Neurological conditions contemplated for treatment by the invention include but are not limited to attention deficit disorder (ADD), autism, dyslexia, and those described infra.

Structural disorders contemplated as amenable to the treatments described herein include malformed organs, omphalocele, cystic dysplastic kidney, Potter's syndrome, urinary obstruction, bladder outlet obstruction, atrial and ventricular septal defect, hypoplastic heart, AV canal, transposition of the great arteries, and coarctation of the aorta.

Brain and skull defects contemplated as amenable to the disclosed invention include anencephaly, spina bifida, porencephalic cyst, holoprosencephaly, and certain forms of hydrocephalus.

As various modifications could be made to the exemplary embodiments, as described above without departing from the scope of the invention, it is intended that all matter contained in the foregoing description shall be interpreted as illustrative, being exemplary in nature rather than limiting. For example, the chelation therapies described above may also be used to diagnose metal toxins in men and detoxify these men prior to their impregnation of their respective partners. Thus, the breadth and scope of the present invention should not be limited by any of the above-described exemplary embodiments, but should be defined only in accordance with the following claims appended hereto and their equivalents.

What is claimed is:

1. A method of determining a cause of a fetal distress comprising:
    delivering an infant from a human female;
    administering at least one or more times a chelating agent or agents, to the human female following delivery of an infant, said agent or agents being capable of sequestering a heavy metal, wherein administering each chelating agent serves as a diagnostic provocation that sequesters a heavy metal, and wherein the urine of the human female is collected for a defined period of time and analyzed for metal content to identify the heavy metal in the human female;
    and correlating said presence of heavy metals with fetal distress.

2. The method of claim 1 wherein the chelating agent is selected from the group consisting of ampicillin, lactate, penicillamine, desferroxamine, Vitamin C, pyruvate, heparin, porphyrins, purines, pyrimidines, RNA, DNA, amino acids, and crown ethers.

3. The method of claim 1 wherein the chelating agent is a proteinaceous chelating agent selected from the group consisting of transferrin, ferritin, meallothionine, albumin and, synthetically designed proteins.

4. The method of claim 1 further comprising the steps of calculating a suitable dosage of a chelating agent and administering the dosage of the chelating agent to the human female prior to or during a subsequent pregnancy, thereby reducing likelihood of a subsequent fetal distress.

5. The method of claim 1 further comprising the step of preparing a fetal distress report based on the analyzing and correlating steps.

6. The method of claim 5 further comprising the step introducing the results of the chelation diagnostic tests in a malpractice case.

7. The method of claim 4 further comprising the step of when the human is a fertile female attempting to achieve pregnancy and having a menstrual cycle with a fertile period and an infertile period and then administering step is restricted to the infertile period of the menstrual cycle.

8. The method of claim 4 further comprising the step of when the human is a fertile female who is pregnant then the calculating step comprises performing a calculation based on the gestational age of the fetus of the pregnant human female.

9. The method of claim 1 further comprising the step of co-administering the chelating agent with mineral supplements.

10. The method of claim 4 further comprising the step of co-administering the chelating agent with mineral supplements.

11. The method of claim 1 wherein the chelating agent is engineered to have a specific binding coefficient and a specificity for particular metals.

12. The method of claim 1 wherein the chelating agent is excretable.

13. The method of claim 1 wherein the levels of heavy metal identified are subclinical.

14. The method of claim 4 further comprising the step of repeating the administration of the dosage of the chelating agent on a fixed schedule.

15. The method of claim 1 wherein the administration of the chelating agent is during lactation.

16. A method of determining a cause of a fetal distress comprising:
  delivering an infant from a human female;
  administering a chelating agent capable of sequestering a heavy metal to the human female following delivering the infant, wherein administering the chelating agent serves as a diagnostic provocation;
  collecting a specimen from the human female following administering a chelating agent wherein the chelating agent has removed by chelation heavy metals from the body of the human female to the specimen of the human female;
  analyzing the specimen for a presence of heavy metals;
  correlating said presence of heavy metals with said fetal distress;
  calculating a suitable dosage of a chelating agent; and
  administering the dosage of the chelating agent to the human female prior to or during a subsequent pregnancy, thereby reducing likelihood of a subsequent fetal distress.

* * * * *

UNITED STATES PATENT AND TRADEMARK OFFICE
CERTIFICATE OF CORRECTION

PATENT NO. : 10,322,100 B2
APPLICATION NO. : 15/437094
DATED : June 18, 2019
INVENTOR(S) : Patrick James Baggot Page 1 of 1

It is certified that error appears in the above-identified patent and that said Letters Patent is hereby corrected as shown below:

In the Specification

Column 11, Line 52, delete "halm" and replace with -- harm --

Column 14, Line 26, delete "tem'" and replace with -- term --

Signed and Sealed this
Second Day of February, 2021

Drew Hirshfeld
*Performing the Functions and Duties of the
Under Secretary of Commerce for Intellectual Property and
Director of the United States Patent and Trademark Office*